(12) United States Patent
Splieth et al.

(10) Patent No.: US 9,421,106 B2
(45) Date of Patent: Aug. 23, 2016

(54) REVERSE SHOULDER BASEPLATE WITH ALIGNMENT GUIDE FOR GLENOSPHERE

(75) Inventors: Roy Splieth, Central Valley, NY (US); James David Lorek, Cary, NC (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/313,487

(22) Filed: Dec. 7, 2011

(65) Prior Publication Data

US 2013/0150973 A1    Jun. 13, 2013

(51) Int. Cl.
*A61F 2/40* (2006.01)
*A61F 2/30* (2006.01)
*A61B 17/80* (2006.01)

(52) U.S. Cl.
CPC ........... *A61F 2/4081* (2013.01); *A61B 17/8052* (2013.01); *A61F 2002/30113* (2013.01); *A61F 2002/30224* (2013.01); *A61F 2002/30332* (2013.01); *A61F 2002/30336* (2013.01); *A61F 2002/30354* (2013.01); *A61F 2002/30357* (2013.01); *A61F 2002/30433* (2013.01); *A61F 2002/30604* (2013.01); *A61F 2002/30784* (2013.01); *A61F 2002/30785* (2013.01); *A61F 2002/4085* (2013.01)

(58) Field of Classification Search
CPC ................ A61F 2/4081; A61F 2/4612; A61F 2/40–2002/4074; A61F 2002/4085; A61F 2/42
USPC ....................... 623/22.11, 22.4, 22.42, 23.11, 623/19.11–19.14
See application file for complete search history.

(56) References Cited

U.S. PATENT DOCUMENTS

| 3,102,536 A | 9/1963 | Rose |
| 3,806,957 A | 4/1974 | Shersher et al. |
| 3,978,528 A | 9/1976 | Crep |
| 4,030,143 A | 6/1977 | Elloy et al. |

(Continued)

FOREIGN PATENT DOCUMENTS

| DE | 10335442 A1 | 2/2005 |
| DE | 202008008565 U1 | 8/2008 |

(Continued)

OTHER PUBLICATIONS

Extended European Search Report for Application No. EP12195588 dated Mar. 1, 2013.

(Continued)

*Primary Examiner* — Christopher D Prone
(74) *Attorney, Agent, or Firm* — Lerner, David, Littenberg, Krumholz & Mentlik, LLP (57) ABSTRACT

Disclosed herein is an implant assembly including an alignment guide for aligning the engagement between a glenosphere and baseplate via a central screw engaged to the baseplate. The glenosphere includes first and second recess portions. The first recess portion of the glenosphere is configured to engage a tapered side surface of the baseplate and the second recess portion of the glenosphere is configured to engage a portion of a head of the central screw projecting outwardly from a top surface of the baseplate when engaged thereto. The portion of the head of the central screw projecting outwardly from the baseplate is slip-fit into the second recess of the glenosphere. This engagement aids the alignment of the glenosphere and the baseplate and helps to ensure the accurate alignment of the tapered engagement of the side surface of the baseplate and the first recess of the glenosphere.

21 Claims, 8 Drawing Sheets

SECTION E-E

(56) References Cited

U.S. PATENT DOCUMENTS

| | | |
|---|---|---|
| 4,040,131 A | 8/1977 | Gristina |
| 4,279,041 A | 7/1981 | Buchholz et al. |
| 4,524,467 A | 6/1985 | DeCarlo, Jr. |
| 4,693,723 A | 9/1987 | Gabard et al. |
| 5,358,526 A | 10/1994 | Tornier |
| 5,462,563 A | 10/1995 | Shearer et al. |
| 5,489,309 A | 2/1996 | Lackey et al. |
| 5,569,263 A | 10/1996 | Hein |
| 5,609,639 A | 3/1997 | Walker |
| 5,609,644 A | 3/1997 | Ashby et al. |
| 5,658,340 A | 8/1997 | Muller et al. |
| 5,702,457 A | 12/1997 | Walch et al. |
| 5,702,470 A | 12/1997 | Menon |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,801 A | 5/1998 | Walker et al. |
| 5,824,106 A | 10/1998 | Fournol |
| 5,879,401 A | 3/1999 | Besemer et al. |
| 5,961,555 A | 10/1999 | Huebner |
| 6,015,437 A | 1/2000 | Stossel |
| 6,033,439 A | 3/2000 | Camino et al. |
| 6,045,582 A | 4/2000 | Prybyla |
| 6,102,953 A | 8/2000 | Huebner |
| 6,120,542 A | 9/2000 | Camino et al. |
| 6,129,764 A | 10/2000 | Servidio |
| 6,168,627 B1 | 1/2001 | Huebner |
| 6,168,628 B1 | 1/2001 | Huebner |
| 6,193,758 B1 | 2/2001 | Huebner |
| 6,197,062 B1 | 3/2001 | Fenlin |
| 6,197,063 B1 | 3/2001 | Dews |
| 6,206,925 B1 | 3/2001 | Tornier |
| 6,217,618 B1 | 4/2001 | Hileman |
| 6,228,120 B1 | 5/2001 | Leonard et al. |
| 6,283,999 B1 | 9/2001 | Rockwood, Jr. |
| 6,368,352 B1 | 4/2002 | Camino et al. |
| 6,485,520 B1 | 11/2002 | Hubach et al. |
| 6,494,913 B1 | 12/2002 | Huebner |
| 6,508,840 B1 | 1/2003 | Rockwood, Jr. et al. |
| 6,508,841 B2 | 1/2003 | Martin et al. |
| 6,520,994 B2 | 2/2003 | Nogarin |
| 6,524,342 B1 | 2/2003 | Muhlhausler et al. |
| 6,530,957 B1 | 3/2003 | Jack |
| 6,589,282 B2 | 7/2003 | Pearl |
| 6,602,292 B2 | 8/2003 | Burkinshaw |
| 6,673,114 B2 | 1/2004 | Hartdegen et al. |
| 6,679,916 B1 | 1/2004 | Frankle et al. |
| 6,719,799 B1 | 4/2004 | Kropf |
| 6,736,852 B2 | 5/2004 | Callaway et al. |
| 6,749,637 B1 | 6/2004 | Bahler |
| 6,761,740 B2 | 7/2004 | Tornier |
| 6,790,234 B1 | 9/2004 | Frankle |
| 6,800,094 B2 | 10/2004 | Burkinshaw |
| 6,818,019 B2 | 11/2004 | Horber |
| 6,887,276 B2 | 5/2005 | Gerbec et al. |
| 6,887,277 B2 | 5/2005 | Rauscher et al. |
| 6,890,358 B2 | 5/2005 | Ball et al. |
| 6,899,736 B1 | 5/2005 | Rauscher et al. |
| 6,942,699 B2 | 9/2005 | Stone et al. |
| 6,953,478 B2 | 10/2005 | Bouttens et al. |
| 6,969,406 B2 * | 11/2005 | Tornier ............ 623/19.13 |
| 6,986,790 B2 | 1/2006 | Ball et al. |
| 7,011,686 B2 | 3/2006 | Ball et al. |
| 7,033,396 B2 | 4/2006 | Tornier |
| 7,044,973 B2 | 5/2006 | Rockwood, Jr. et al. |
| 7,097,663 B1 | 8/2006 | Nicol et al. |
| 7,108,405 B2 | 9/2006 | Matts et al. |
| 7,108,719 B2 | 9/2006 | Horber |
| 7,166,132 B2 | 1/2007 | Callaway et al. |
| 7,169,184 B2 | 1/2007 | Dalla Pria et al. |
| 7,175,663 B1 | 2/2007 | Stone |
| 7,175,664 B1 | 2/2007 | Lakin |
| 7,186,269 B2 | 3/2007 | Cyprien et al. |
| 7,238,207 B2 | 7/2007 | Blatter et al. |
| 7,238,208 B2 | 7/2007 | Camino et al. |
| 7,241,314 B1 | 7/2007 | Winslow |
| 7,297,163 B2 | 11/2007 | Huebner |
| 7,303,585 B2 | 12/2007 | Horber |
| 7,309,360 B2 | 12/2007 | Tornier et al. |
| 7,329,284 B2 | 2/2008 | Maroney et al. |
| 7,338,528 B2 | 3/2008 | Stone et al. |
| 7,425,214 B1 | 9/2008 | McCarthy et al. |
| 7,445,638 B2 | 11/2008 | Beguin et al. |
| 7,462,197 B2 | 12/2008 | Tornier et al. |
| 7,465,319 B2 | 12/2008 | Tornier |
| 7,470,287 B2 | 12/2008 | Tornier et al. |
| 7,531,003 B2 | 5/2009 | Reindel |
| 7,537,618 B2 | 5/2009 | Collazo |
| 7,544,211 B2 | 6/2009 | Rochetin |
| 7,608,109 B2 | 10/2009 | Dalla Pria |
| 7,611,539 B2 | 11/2009 | Bouttens et al. |
| 7,621,961 B2 | 11/2009 | Stone |
| 7,648,530 B2 | 1/2010 | Habermeyer et al. |
| 7,678,150 B2 | 3/2010 | Tornier et al. |
| 7,753,959 B2 | 7/2010 | Berelsman et al. |
| 7,758,650 B2 | 7/2010 | Dews et al. |
| 7,785,370 B2 | 8/2010 | Collazo |
| 7,819,923 B2 | 10/2010 | Stone et al. |
| 7,854,768 B2 | 12/2010 | Wiley et al. |
| 7,918,892 B2 | 4/2011 | Huebner |
| 7,922,769 B2 | 4/2011 | Deffenbaugh et al. |
| 7,951,204 B2 | 5/2011 | Chambat et al. |
| 7,959,680 B2 | 6/2011 | Stone et al. |
| 8,002,838 B2 | 8/2011 | Klotz |
| 8,002,841 B2 | 8/2011 | Hasselman |
| 8,062,376 B2 | 11/2011 | Shultz et al. |
| 8,070,820 B2 | 12/2011 | Winslow et al. |
| 8,105,385 B2 | 1/2012 | Maroney et al. |
| 8,118,875 B2 | 2/2012 | Rollet |
| 8,118,876 B2 | 2/2012 | Gupta et al. |
| 8,137,407 B2 | 3/2012 | Todd et al. |
| 8,142,510 B2 | 3/2012 | Lee et al. |
| 8,147,557 B2 | 4/2012 | Lee et al. |
| 8,157,866 B2 | 4/2012 | Winslow et al. |
| 8,182,542 B2 | 5/2012 | Ferko |
| 8,192,497 B2 | 6/2012 | Ondrla |
| 8,231,682 B2 | 7/2012 | Lafosse et al. |
| 8,236,059 B2 | 8/2012 | Stone et al. |
| 8,241,366 B2 | 8/2012 | Roche et al. |
| 8,246,687 B2 | 8/2012 | Katrana et al. |
| 8,273,130 B2 | 9/2012 | Gradl |
| 8,277,511 B2 | 10/2012 | Tornier et al. |
| 8,303,665 B2 | 11/2012 | Tornier et al. |
| 8,323,347 B2 | 12/2012 | Guederian et al. |
| 8,328,874 B2 | 12/2012 | Lee |
| 8,337,563 B2 | 12/2012 | Roche et al. |
| 8,343,226 B2 | 1/2013 | Nogarin et al. |
| 8,361,157 B2 | 1/2013 | Bouttens et al. |
| 8,419,798 B2 | 4/2013 | Ondrla et al. |
| 8,444,698 B2 | 5/2013 | Klotz et al. |
| 8,454,702 B2 | 6/2013 | Smits et al. |
| 8,460,390 B2 | 6/2013 | Biss et al. |
| 8,545,504 B2 | 10/2013 | Durand-Allen et al. |
| 8,545,511 B2 | 10/2013 | Splieth et al. |
| 8,562,686 B2 | 10/2013 | Klotz et al. |
| 8,591,591 B2 | 11/2013 | Winslow et al. |
| 8,608,805 B2 | 12/2013 | Forrer et al. |
| 8,617,249 B2 | 12/2013 | Emami |
| 8,623,092 B2 | 1/2014 | Bickley et al. |
| 8,623,093 B2 | 1/2014 | Dickerson |
| 8,632,603 B2 | 1/2014 | Hodorek et al. |
| 8,647,387 B2 | 2/2014 | Winslow |
| 8,663,334 B2 | 3/2014 | Viscardi et al. |
| 2001/0007957 A1 | 7/2001 | Martin et al. |
| 2001/0011192 A1 | 8/2001 | Ondrla et al. |
| 2001/0011193 A1 | 8/2001 | Nogarin |
| 2001/0049561 A1 | 12/2001 | Dews et al. |
| 2001/0053935 A1 | 12/2001 | Hartdegen et al. |
| 2002/0016634 A1 | 2/2002 | Maroney et al. |
| 2002/0099445 A1 | 7/2002 | Maroney et al. |
| 2002/0120339 A1 | 8/2002 | Callaway et al. |
| 2002/0128719 A1 | 9/2002 | Burkinshaw |
| 2003/0014119 A1 | 1/2003 | Capon et al. |

(56) References Cited

U.S. PATENT DOCUMENTS

| | | |
|---|---|---|
| 2003/0028253 A1 | 2/2003 | Stone et al. |
| 2003/0099519 A1 | 5/2003 | Robinson et al. |
| 2003/0114933 A1 | 6/2003 | Bouttens et al. |
| 2003/0149486 A1 | 8/2003 | Huebner |
| 2003/0158605 A1 | 8/2003 | Tornier |
| 2004/0030394 A1 | 2/2004 | Horber |
| 2004/0030396 A1 | 2/2004 | Horber |
| 2004/0039449 A1 | 2/2004 | Tornier |
| 2004/0059424 A1 | 3/2004 | Guederian et al. |
| 2004/0064187 A1 | 4/2004 | Ball et al. |
| 2004/0064188 A1 | 4/2004 | Ball et al. |
| 2004/0064190 A1 | 4/2004 | Ball et al. |
| 2004/0143336 A1 | 7/2004 | Burkinshaw |
| 2004/0143337 A1 | 7/2004 | Burkinshaw |
| 2004/0186579 A1 | 9/2004 | Callaway et al. |
| 2004/0210317 A1 | 10/2004 | Maroney et al. |
| 2004/0220673 A1 | 11/2004 | Pria |
| 2004/0220674 A1 | 11/2004 | Pria |
| 2004/0267370 A1 | 12/2004 | Ondrla |
| 2005/0033443 A1 | 2/2005 | Blatter et al. |
| 2005/0085921 A1 | 4/2005 | Gupta et al. |
| 2005/0113931 A1 | 5/2005 | Horber |
| 2005/0128755 A1 | 6/2005 | Matts et al. |
| 2005/0143829 A1 | 6/2005 | Ondrla et al. |
| 2005/0256583 A1 | 11/2005 | Bouttens et al. |
| 2005/0278030 A1 | 12/2005 | Tornier et al. |
| 2005/0278032 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0020344 A1* | 1/2006 | Shultz et al. ............... 623/19.12 |
| 2006/0030946 A1 | 2/2006 | Ball et al. |
| 2006/0069445 A1 | 3/2006 | Ondrla et al. |
| 2006/0079963 A1 | 4/2006 | Hansen |
| 2006/0129247 A1 | 6/2006 | Brown et al. |
| 2006/0142872 A1 | 6/2006 | Klotz et al. |
| 2006/0161260 A1 | 7/2006 | Thomas et al. |
| 2006/0200247 A1 | 9/2006 | Charrois |
| 2006/0200248 A1 | 9/2006 | Beguin et al. |
| 2006/0229730 A1 | 10/2006 | Railey et al. |
| 2007/0050040 A1 | 3/2007 | Guederian et al. |
| 2007/0078519 A1 | 4/2007 | Klotz |
| 2007/0100458 A1 | 5/2007 | Dalla Pria |
| 2007/0112430 A1 | 5/2007 | Simmen et al. |
| 2007/0118230 A1 | 5/2007 | Callaway et al. |
| 2007/0156246 A1 | 7/2007 | Meswania et al. |
| 2007/0173945 A1 | 7/2007 | Wiley et al. |
| 2007/0179624 A1 | 8/2007 | Stone et al. |
| 2007/0198094 A1 | 8/2007 | Berelsman et al. |
| 2007/0225820 A1 | 9/2007 | Thomas et al. |
| 2007/0243045 A1 | 10/2007 | Gaska |
| 2007/0244563 A1 | 10/2007 | Roche et al. |
| 2007/0299527 A1 | 12/2007 | McCleary et al. |
| 2008/0221622 A1 | 9/2008 | Triplett et al. |
| 2008/0228281 A1 | 9/2008 | Forrer et al. |
| 2008/0275507 A1 | 11/2008 | Triplett et al. |
| 2008/0294268 A1 | 11/2008 | Baum et al. |
| 2008/0306600 A1 | 12/2008 | Huebner |
| 2009/0062923 A1 | 3/2009 | Swanson |
| 2009/0099662 A1 | 4/2009 | Splieth et al. |
| 2009/0149961 A1* | 6/2009 | Dallmann ............... 623/19.11 |
| 2009/0164021 A1 | 6/2009 | Dallmann |
| 2009/0171462 A1 | 7/2009 | Poncet et al. |
| 2009/0192621 A1 | 7/2009 | Winslow et al. |
| 2009/0210065 A1 | 8/2009 | Nerot et al. |
| 2009/0216332 A1 | 8/2009 | Splieth et al. |
| 2009/0270993 A1 | 10/2009 | Maisonneuve et al. |
| 2009/0281630 A1 | 11/2009 | Delince et al. |
| 2009/0287309 A1 | 11/2009 | Walch et al. |
| 2010/0023068 A1 | 1/2010 | Bouttens et al. |
| 2010/0049327 A1 | 2/2010 | Isch et al. |
| 2010/0057210 A1 | 3/2010 | Ondrla |
| 2010/0087927 A1 | 4/2010 | Roche et al. |
| 2010/0125336 A1 | 5/2010 | Johnson et al. |
| 2010/0161065 A1 | 6/2010 | Williams, Jr. et al. |
| 2010/0161066 A1 | 6/2010 | Iannotti et al. |
| 2010/0211178 A1 | 8/2010 | Nogarin et al. |
| 2010/0222886 A1 | 9/2010 | Wiley et al. |
| 2010/0228352 A1 | 9/2010 | Courtney, Jr. et al. |
| 2010/0234959 A1 | 9/2010 | Roche et al. |
| 2011/0054624 A1 | 3/2011 | Iannotti |
| 2011/0060417 A1 | 3/2011 | Simmen et al. |
| 2011/0082557 A1 | 4/2011 | Mutchler et al. |
| 2011/0098822 A1 | 4/2011 | Walch et al. |
| 2011/0106267 A1 | 5/2011 | Grant |
| 2011/0118846 A1 | 5/2011 | Katrana et al. |
| 2011/0153023 A1 | 6/2011 | Deffenbaugh et al. |
| 2011/0178604 A1 | 7/2011 | Porter |
| 2011/0196491 A1 | 8/2011 | Huebner |
| 2011/0295376 A1 | 12/2011 | Winslow |
| 2012/0029647 A1 | 2/2012 | Winslow et al. |
| 2012/0179262 A1 | 7/2012 | Metcalfe et al. |
| 2012/0191201 A1 | 7/2012 | Smits et al. |
| 2012/0209392 A1 | 8/2012 | Angibaud et al. |
| 2012/0221112 A1 | 8/2012 | Lappin |
| 2012/0253467 A1 | 10/2012 | Frankle |
| 2012/0259334 A1 | 10/2012 | Splieth et al. |
| 2012/0265315 A1 | 10/2012 | Kusogullari et al. |
| 2012/0271425 A1 | 10/2012 | Maurer |
| 2012/0271426 A1 | 10/2012 | Roche et al. |
| 2012/0277880 A1 | 11/2012 | Winslow et al. |
| 2012/0303130 A1 | 11/2012 | Winslow et al. |
| 2013/0006369 A1 | 1/2013 | Wiley et al. |
| 2013/0060341 A1 | 3/2013 | Tornier et al. |
| 2013/0090736 A1 | 4/2013 | Katrana et al. |
| 2013/0197650 A1 | 8/2013 | Smits et al. |
| 2013/0197651 A1 | 8/2013 | McDaniel et al. |
| 2013/0197652 A1 | 8/2013 | Ekelund et al. |
| 2013/0204375 A1 | 8/2013 | Winslow et al. |
| 2013/0245775 A1 | 9/2013 | Metcalfe |
| 2013/0261750 A1 | 10/2013 | Lappin |
| 2013/0267960 A1 | 10/2013 | Groh |
| 2013/0282129 A1 | 10/2013 | Phipps |
| 2013/0325130 A1 | 12/2013 | Viscardi et al. |
| 2013/0325131 A1 | 12/2013 | Roche et al. |
| 2013/0325133 A1 | 12/2013 | Viscardi et al. |
| 2013/0325134 A1 | 12/2013 | Viscardi et al. |
| 2014/0018927 A1 | 1/2014 | De Wilde et al. |
| 2014/0039633 A1 | 2/2014 | Roche et al. |
| 2014/0039634 A1 | 2/2014 | Klotz |

FOREIGN PATENT DOCUMENTS

| | | |
|---|---|---|
| EP | 1314407 A1 | 5/2003 |
| EP | 1520560 | 4/2005 |
| EP | 1656910 A1 | 5/2006 |
| EP | 2047827 A1 | 4/2009 |
| EP | 2201912 A1 | 6/2010 |
| FR | 2689756 | 10/1993 |
| FR | 2699400 | 6/1994 |
| GB | 2001247 A | 1/1979 |
| GB | 2405346 A | 3/2005 |
| WO | 0147442 A1 | 7/2001 |
| WO | 2005032430 | 4/2005 |
| WO | 2007031575 A1 | 3/2007 |
| WO | 2007032820 | 4/2007 |
| WO | 2007084939 | 7/2007 |
| WO | 2008000928 A2 | 1/2008 |

OTHER PUBLICATIONS

Extended European Search Report for Application No. 12183703 dated Jan. 30, 2013.
Reverse Shoulder Prosthesis, Surgical Technique, Encore, 2005.
Delta Reverse Shoulder System, Surgical Technique, DePuy 2004.
European Search Report, EP 10156704, dated Jun. 14, 2010.
Extended European Search Report for Application No. EP13169019 dated Jul. 26, 2013.

* cited by examiner

SECTION A-A

SECTION B-B

SECTION D-D
FIG. 5C

SECTION E-E
FIG. 7D

REVERSE SHOULDER BASEPLATE WITH ALIGNMENT GUIDE FOR GLENOSPHERE

FIELD OF THE TECHNOLOGY

The present invention relates to an alignment guide for reverse shoulder arthroplasty (RSA), and in particular it relates to such a guide for aligning the engagement between a glenosphere and baseplate via a central screw engaged to the baseplate.

BACKGROUND OF THE INVENTION

Many existing reverse shoulder systems (RSA) require a baseplate and a glenosphere. These systems generally differ from one another in how the baseplate is fastened to the glenoid cavity and how the glenosphere becomes engaged to the baseplate. In some systems, the baseplate may be fastened to the glenoid cavity of the scapula by a plurality of screws and a glenosphere having a convex joint surface may be screwed into the baseplate using an axial threaded feature and/or taper locked to a periphery of the baseplate. In other systems, the glenosphere may engage the baseplate solely via a taper connection. Generally, a compression fit is not preferable between the glenosphere and baseplate due to the potential need for separating the two components once engaged to one another.

In cases where the glenosphere becomes engaged to the baseplate through either a threaded or taper connection, the glenosphere and baseplate may become separated after a certain length of time. This may cause the glenosphere to tilt with respect to the baseplate or in some cases even completely separate therefrom. In either situation, the baseplate and glenosphere become misaligned.

Some systems include first fastening a central screw to a glenosphere and then guiding the connection between the baseplate and glenosphere via the central screw. Guiding the connection between the baseplate and glenosphere is generally an important consideration due to minimal access and visibility that the surgeon may have during a RSA procedure. Access to the baseplate is generally narrow making it relatively difficult for the surgeon to have the visibility needed to correctly align the engagement between a baseplate and glenosphere.

BRIEF SUMMARY OF THE INVENTION

One embodiment in accordance with a first aspect of the present invention is an implant assembly including first, second and third components. The first component is preferably a baseplate, the second component is preferably a glenosphere, and the third component is preferably a central screw. First component of the implant assembly preferably includes a top surface, a bottom surface, a side surface connecting the top and bottom surfaces, and at least one borehole extending through the top and bottom surfaces. Second component of the implant assembly preferably includes first and second circumferential recesses, the first circumferential recess defining a tapered wall having a minimum diameter at a base of the tapered wall, the second circumferential recess defining a circumferential wall having a constant diameter, the constant diameter of the circumferential wall being less than the minimum diameter of the tapered wall, the first and second circumferential recesses being in communication with one another. Third component of the implant assembly preferably includes a head portion and a body portion, the third component configured to be received at least partially within the at least one borehole of the first component. At least a portion of the head portion of the third component extends outwardly from the top surface of the first component when the third component is engaged to the at least one borehole of the first component such that the head portion can be slip-fit into the second circumferential recess of the second component and into engagement with the circumferential wall thereof, thereby guiding the engagement of the side surface of the first component into the first circumferential recess and into engagement with the tapered wall of the second component.

In another embodiment of the first aspect of the present invention the top surface of the second component is substantially flat and the bottom surface is convex. The side surface of the first component is preferably tapered and forms a circumferential perimeter of the first component, the side surface having a central longitudinal axis. In some embodiments, the implant assembly includes a plurality of baseplates having variable thicknesses connecting the top and bottom surfaces thereof.

In yet another embodiment of the first aspect of the present invention the at least one borehole of the first component has a central axis that is coaxial with the central longitudinal axis of the side surface of the first component.

In yet still another embodiment of the first aspect of the present invention the implant assembly further comprises a plurality of boreholes extending through the top and bottom surfaces of the first component that are equally spaced around a perimeter of the top and bottom surfaces, the boreholes adapted to receive screws for fixing the first component to a glenoid cavity of a patient. Each of the plurality of boreholes preferably includes a ramp portion adapted to receive and engage a head of a fixation screw. Each of the plurality of boreholes can either be straight or angled from the top surface of the baseplate.

In still yet another embodiment of the first aspect of the present invention the third component further includes a neck portion that is tapered and at least partially threaded, and the at least one borehole includes a threaded portion adapted to engage the at least partially threaded portion of the third component. Preferably, the head portion of the third component has a circumferential side surface and at least a portion of the body portion of the third component is threaded.

In still yet another embodiment of the first aspect of the present invention the second component has a semispherical convex outer surface and the second component has a bore hole through an apex portion thereof. The borehole through the apex portion of the second component is preferably at least partially threaded.

In still yet another embodiment of the first aspect of the present invention the tapered wall and the circumferential wall of the second component each have a longitudinal axis therethrough, the longitudinal axes being coaxial. Preferably, when the first component is engaged to the second component, the central axis of the at least one borehole is coaxial with the longitudinal axes of the tapered wall and the circumferential wall.

One embodiment in accordance with a second aspect of the present invention is an implant assembly including first, second and third components. The first component preferably has a top surface, a bottom surface, a side surface connecting the top and bottom surfaces, and at least one borehole extending through the top and bottom surfaces, the distance between the top surface and bottom surface defining a first height. The second component preferably has first and second circumferential recesses, the first circumferential recess defining a tapered wall having a second height substantially equal to the first height, the second circumferential recess defining a circumferential wall having a third height greater than the second height of the tapered wall, the first and second circumferential recesses being in communication with one another. The third component has a head portion and a body portion, the third component configured to be received at least partially within the at least one borehole of the first component. The third component when engaged to the at least one borehole of the first component the head portion thereof extends outwardly from the top surface of the first component in an amount substantially equal to the third height, and at least a portion of the head portion of the third component is located within the second circumferential recess of the second component and is in engagement with the circumferential wall when at least a portion of the side surface of the first component is located within the first circumferential recess and is in engagement with the tapered wall of the second component.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

As used herein, when referring to bones or other parts of the body, the term "proximal" means closer to the heart and the term "distal" means more distant from the heart. The term "inferior" means lower or bottom and the term "superior" means upper or top. The term "anterior" means towards the front part of the body or the face and the term "posterior" means toward the back of the body. The term "medial" means toward the midline of the body and the term "lateral" means away from the midline of the body.

Figure 1:
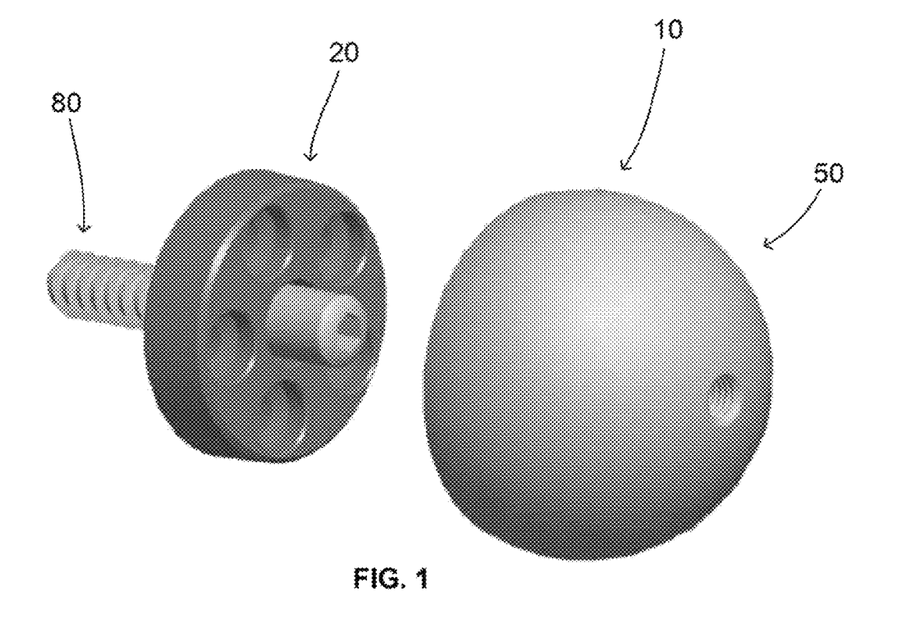
FIG. 1 is an exploded view of an implant system showing a two-piece construct prior to assembly with a glenosphere.

Referring to FIG. 1, there is shown an exploded view of an embodiment of an implant assembly of the present invention designated generally by reference numeral 10. As shown in this figure, implant assembly 10 includes a first component or baseplate 20, a second component or glenosphere 50, and a third component or central screw 80.

Figure 2A:
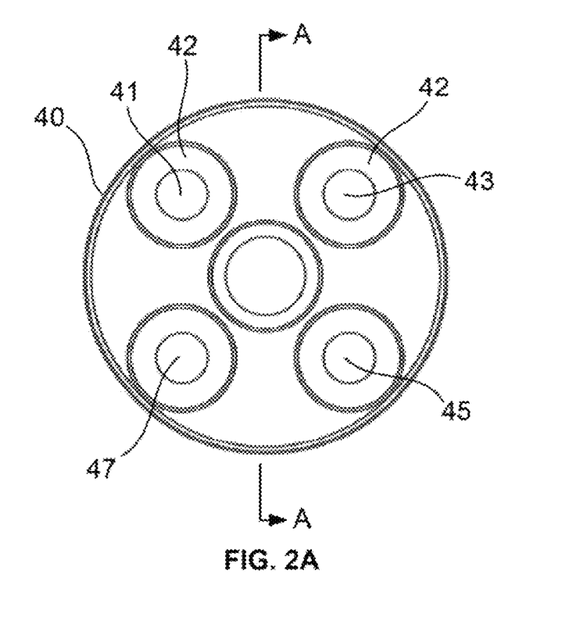
FIG. 2A is a front view of one embodiment of a baseplate of the present invention.
Figure 2B:
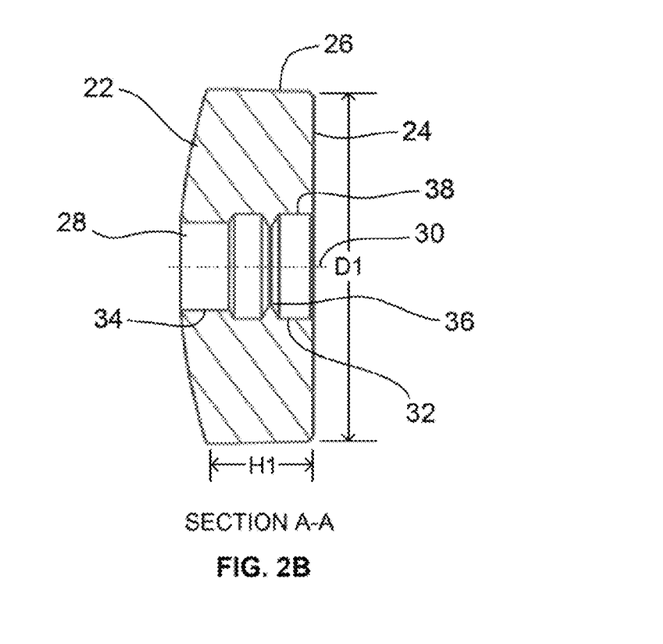
FIG. 2B is a cross-sectional side view taken along line A-A of the baseplate shown in FIG. 2A.
Figure 2C:
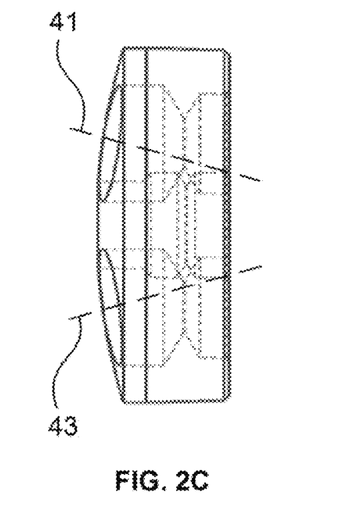
FIG. 2C is an alternate side view of the baseplate shown in FIG. 2A.

Referring to FIGS. 2A-2C, there is shown one embodiment of baseplate 20 of the present invention. Baseplate 20 includes a bottom surface 22, a top surface 24, and a tapered side surface 26 connecting the bottom and top surfaces, the side surface 26 defining a height H1 and a having a minimum diameter D1 defined by a perimeter of top surface 24. A central bore hole 28 extends through bottom and top surfaces 22, 24, the central bore hole 28 having a longitudinal axis 30.

As shown in FIG. 2B, bore hole 28 preferably includes a first diameter 32 and a second diameter 34 with the first diameter being larger than the second diameter. An intermediate portion 36 preferably separates first and second diameters 32, 34, the intermediate portion formed preferably as a singular thread projecting outwardly from a wall 38 of first diameter 32 of central bore hole 28.

Bottom surface 22 of baseplate 20 is generally convex, while top surface 24 is generally flat. Disposed around and adjacent a perimeter or circumference 40 formed by side surface 26 of baseplate 20 are a plurality of screw receiving apertures 42. While baseplate 20 as shown in FIG. 2A, includes four screw receiving apertures 42, baseplate 20 may include less or more than four screw receiving apertures 42. As shown in FIG. 2A, apertures 42 moving in a clockwise direction include a longitudinal axis 41, 43, 45, or 47, respectively. Longitudinal axes 41, 43, 45 and 47 are preferably angled from longitudinal axis 30 between 15° and 75° as shown in FIG. 2C, for example. Longitudinal axes 41, 43, 45 and 47 may each be angled from longitudinal axis 30 that same amount of degrees or each may be angled from longitudinal axis 30 a different amount of degrees. In some embodiments, longitudinal axes 41, 43, 45 and 47 may be parallel to longitudinal axis 30 of bore hole 28.

Figure 3A:
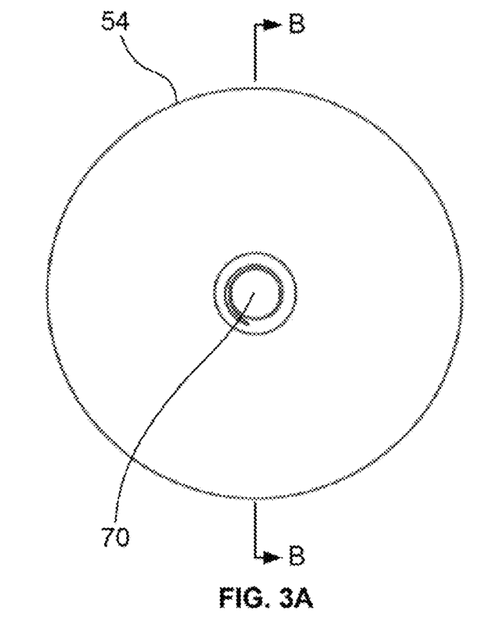
FIG. 3A is a back view of one embodiment of a glenosphere of the present invention.
Figure 3B:
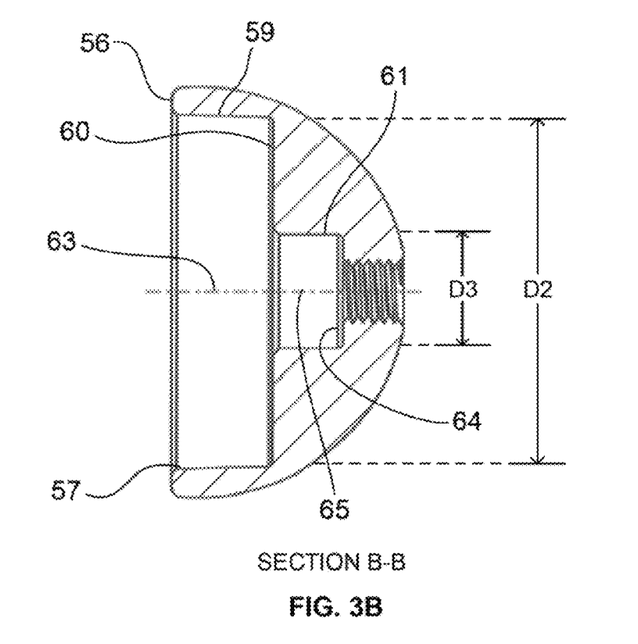
FIG. 3B is a cross-sectional side view taken along line B-B of the glenosphere shown in FIG. 3A.
Figure 3C:
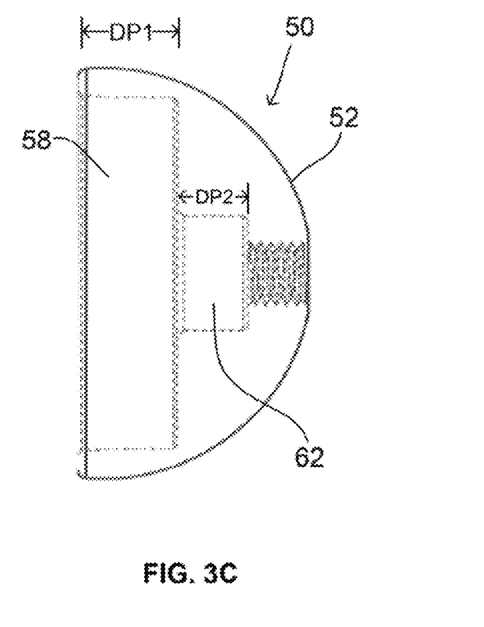
FIG. 3C is an alternate side view of the glenosphere shown in FIG. 3A.

Referring to FIGS. 3A-3C, there is shown one embodiment of a second component or glenosphere 50 of the present invention. Glenosphere 50 includes a hemispherical or semi-spherical outer surface 52 having a perimeter 54 forming an outer diameter of a bottom surface 56. Starting at bottom surface 56 and projecting inwardly therefrom is a first circumferential recess 58 having a depth DP1 slightly larger than height H1 of baseplate 20. In one embodiment, depth DP1 may be substantially equivalent to height H1. First circumferential recess 58 defines a tapered wall 59 having a maximum diameter defining an outer perimeter 57 and a minimum diameter defining a first base portion 60 of the tapered wall. First circumferential recess 58 terminates at first base portion 60 of tapered wall 59.

Starting at first base portion 60 and projecting inwardly therefrom is a second circumferential recess 62 having a depth DP2. Second circumferential recess 62 defines a circumferential wall 61 having a constant diameter. Second circumferential recess 62 terminates at a base portion of circumferential wall 61 at a second base portion 64. The constant diameter of the circumferential wall 61 is preferably less than the minimum diameter of tapered wall 59. The first and second circumferential recesses 58 and 62 are in communication with one another. First circumferential recess includes a longitudinal axis 63 and second circumferential recess includes a longitudinal axis 65, the longitudinal axes 63, 65 of first and second circumferential recesses are coaxial. In other embodiments, longitudinal axes 63 and 65 may be offset from one another.

As shown in FIGS. 3A-3C, located at a polar or apex portion of glenosphere 50 is a threaded bore 70. Threaded bore 70 is in communication with first and second circumferential recesses 58 and 62. In other embodiments, threaded bore 70 is a recess formed in outer surface 52 and is not in communication with either first or second circumferential recess 58 and 62. In other embodiments, bore 70 is only partially threaded about a length thereof.

Figure 4A:
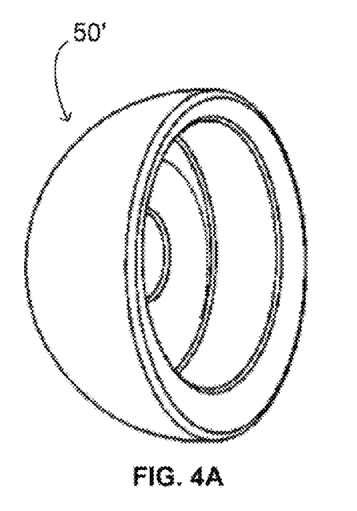
FIG. 4A is a perspective view of an alternate embodiment of a glenosphere of the present invention.
Figure 4B:
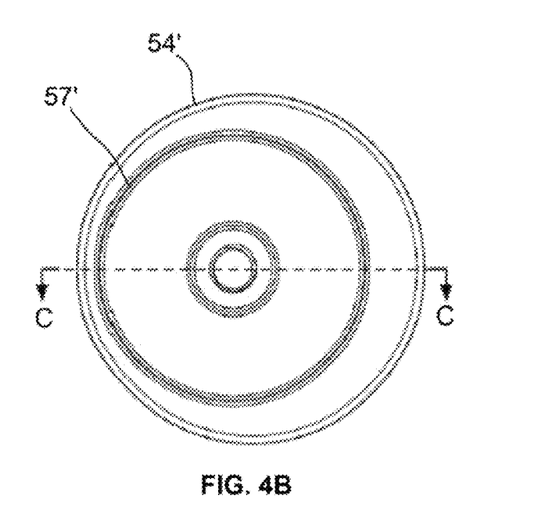
FIG. 4B is a front view of the glenosphere shown in FIG. 4A.
Figure 4C:
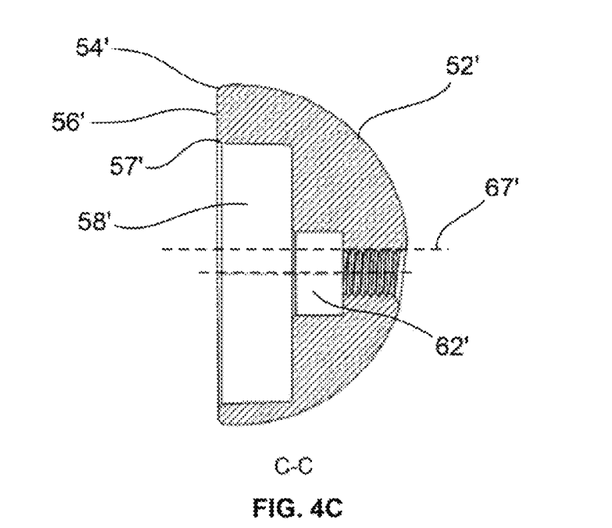
FIG. 4C is a cross-sectional side view taken along line C-C of the glenosphere shown in FIG. 4B.

Referring to FIGS. 4A-4C, there is shown another embodiment of glenosphere 50 of the present invention denoted as 50'. Glenosphere 50' includes all of the same features as glenosphere 50 except that the first and second circumferential recesses 58', 62' are offset from threaded bore 70' of glenosphere 50'. First circumferential recess 58' includes a longitudinal axis 63' and second circumferential recess 62' includes a longitudinal axis 65', the longitudinal axes 63', 65' of first and second circumferential recesses are coaxial. Glenosphere 50' includes a hemispherical or semispherical outer surface 52' having a perimeter 54' forming an outer diameter of a bottom surface 56'. Perimeter 54' includes a longitudinal axis 67' that is offset from longitudinal axes 63', 65' of first and second circumferential recesses 58', 62'.

Figure 5A:
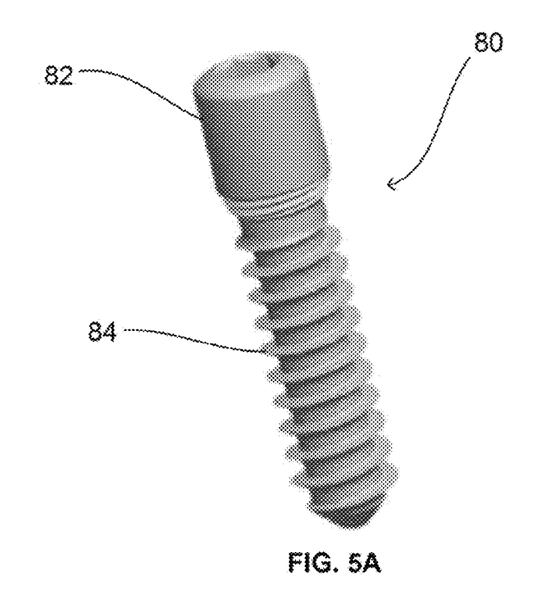
FIG. 5A is a perspective view of one embodiment of a central screw of the present invention.
Figure 5B:
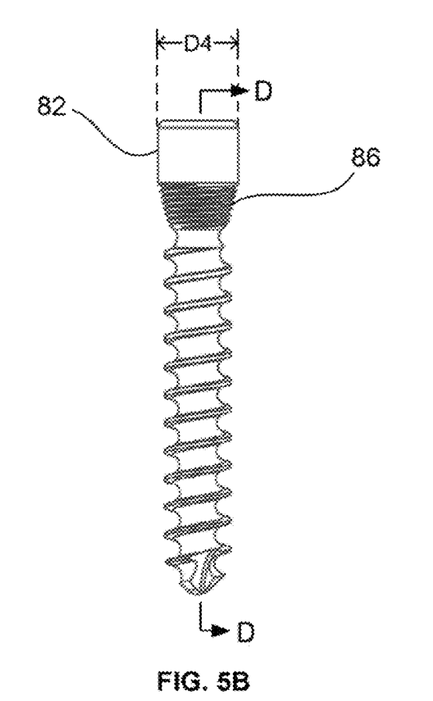
FIG. 5B is a side plan view of the central screw shown in FIG. 5A.
Figure 5C:
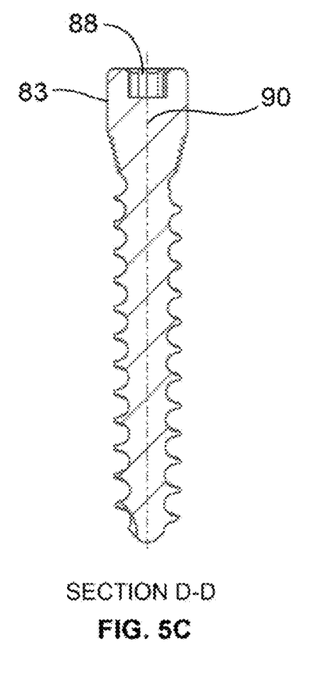
FIG. 5C is a cross-sectional side view taken along line D-D of the central screw shown in FIG. 5B.

Referring to FIGS. 5A-5C, there is shown one embodiment of a third component or central screw 80 of the present invention. Central screw 80 includes a head portion 82, a body portion 84, a neck portion 86 and a longitudinal axis 90. Head portion 82 includes a circumferential side surface 83 defining a perimeter with a diameter D4. Body portion 84 of central screw 80 is preferably threaded. Neck portion 86 is preferably tapered and threaded. Central screw 80 further includes an engagement portion 88 for receiving an adjustment tool such as a screwdriver, for example.

Figure 6A:
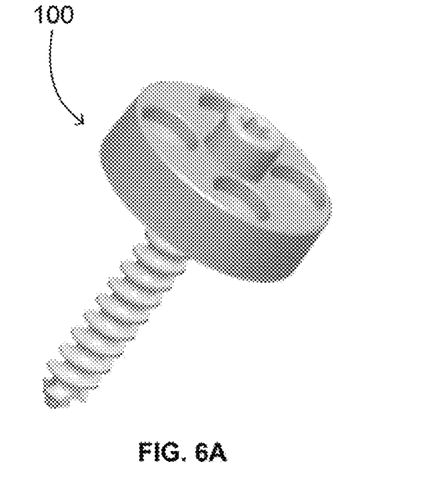
FIG. 6A is a perspective view of one embodiment of a two-piece construct of the present invention including an assembled baseplate and central screw.
Figure 6B:
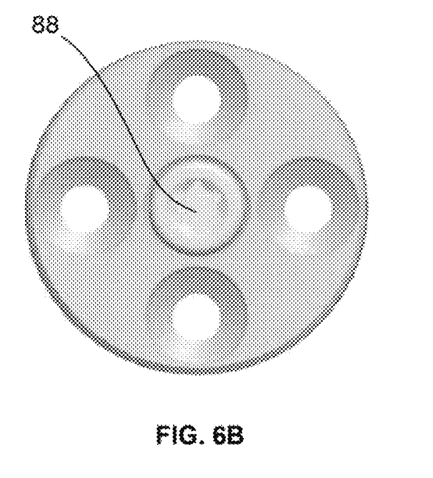
FIG. 6B is a top view of the two-piece construct shown in FIG. 6A.
Figure 6C:
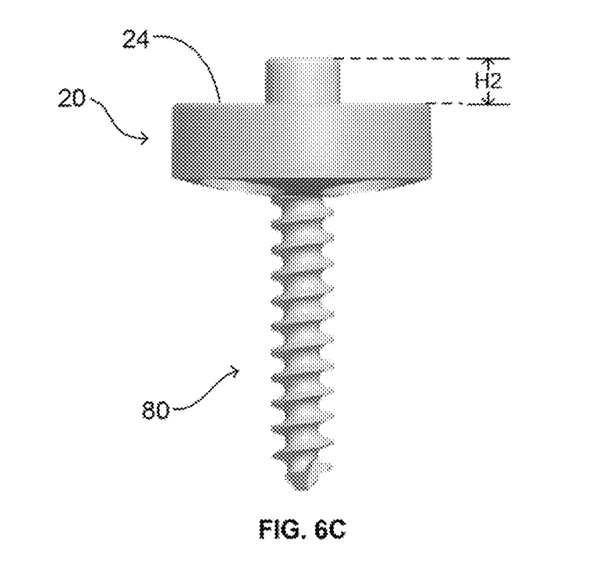
FIG. 6C is a side view of the two-piece construct shown in FIG. 6A.
Figure 7A:
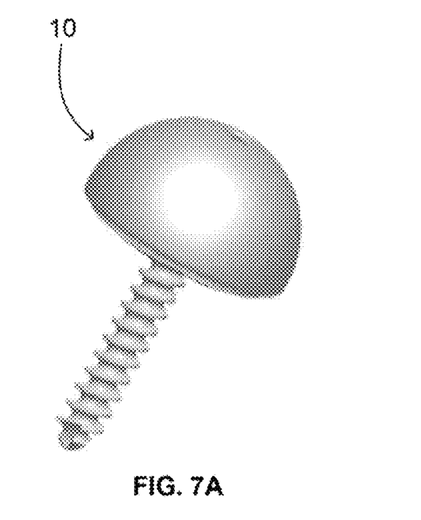
FIG. 7A is a perspective view of one embodiment of an implant assembly of the present invention showing a two-piece construct assembled to a glenosphere.
Figure 7B:
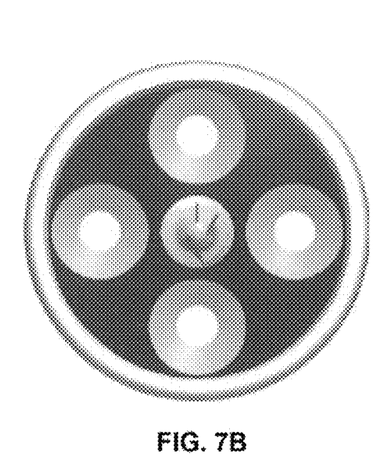
FIG. 7B is a bottom view of the implant assembly shown in FIG. 7A.
Figure 7C:
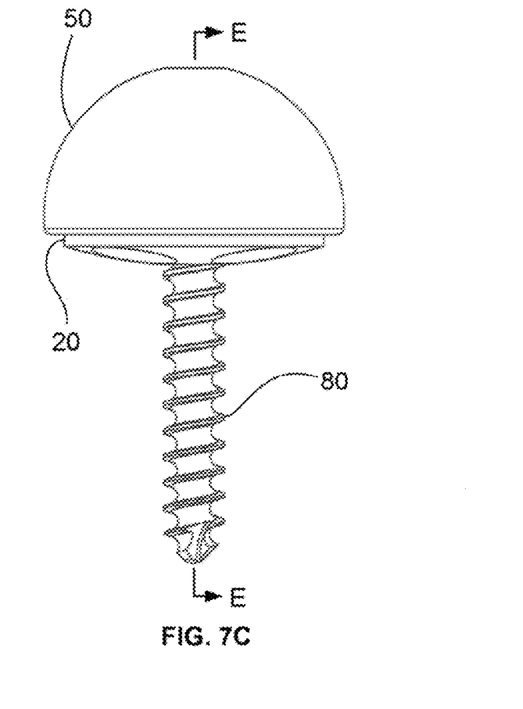
FIG. 7C is a side view of the implant assembly shown in FIG. 7A.
Figure 7D:
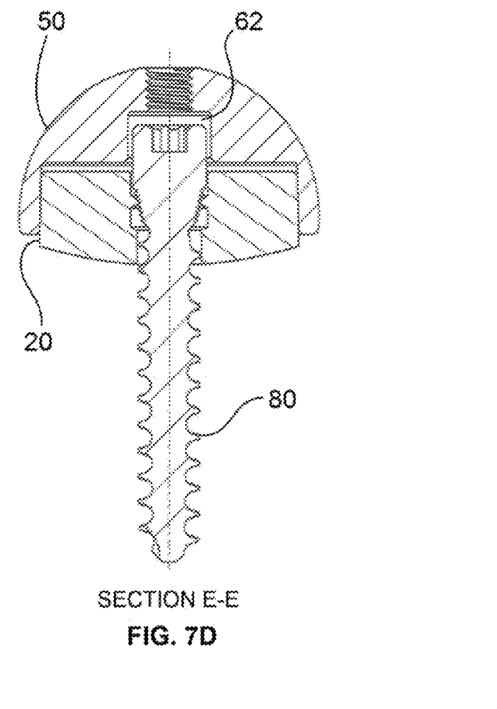
FIG. 7D is a cross-sectional view taken along line E-E of the implant assembly shown in FIG. 7C.

In reference to FIGS. 6A-6C there is shown one embodiment of a two-piece construct 100 including an assembled baseplate 20 and central screw 80. When assembled, a portion of head portion 82 of central screw 80 projects outwardly from outer surface 24 of baseplate 20 a height H2. Depending on the configuration of first and second circumferential recesses and 62 of glenosphere 50, namely depths DP1 and DP2, respectively, the height H2 may vary.

In reference to FIGS. 7A-7D there is shown implant assembly 10 with baseplate 20, glenosphere 50, and central screw 80 all being assembled together. The alignment guide of implant assembly 10 serves to enable a more efficient and reproducible alignment between glenosphere 50 and baseplate 20 during RSA. In one method of the invention, after baseplate is secured to a patient's scapula by fixation screws, glenosphere 50 may be coupled thereto. It is important for the alignment of glenosphere 50 to be accurate on the baseplate 20. In other words longitudinal axis 30 of baseplate 20 and longitudinal axis 63 of glenosphere should be coaxial when implant assembly 10 is in an assembled position.

The diameter D4 of head portion 82 of central screw 80 is preferably 8 mm, but may be as little as 2 mm and as much as 14 mm, for example. When central screw 80 is assembled to baseplate 20, head portion 82 of central 80 preferably protrudes from top surface 24 of baseplate 20 approximately 5 mm. Second circumferential recess 62 of glenosphere 50 has a diameter of approximately 9 mm (just slightly more than the diameter of head portion 82 of central screw 80) and a depth of 5.4 mm (just slightly more than the amount head portion 82 of central screw 80 protrudes from top surface 24 of baseplate 20).

Implant assembly 10 provides a surgeon or other operating room personnel with improved tactile feel and axial alignment when introducing glenosphere 50 onto baseplate 20 during final implantation. Reduction of surgery time is preferably a benefit attributable to implant assembly 10, which also has the potential to reduce the amount of time a surgeon needs to implant this device with a one step procedure strategy.

Figure 8A:
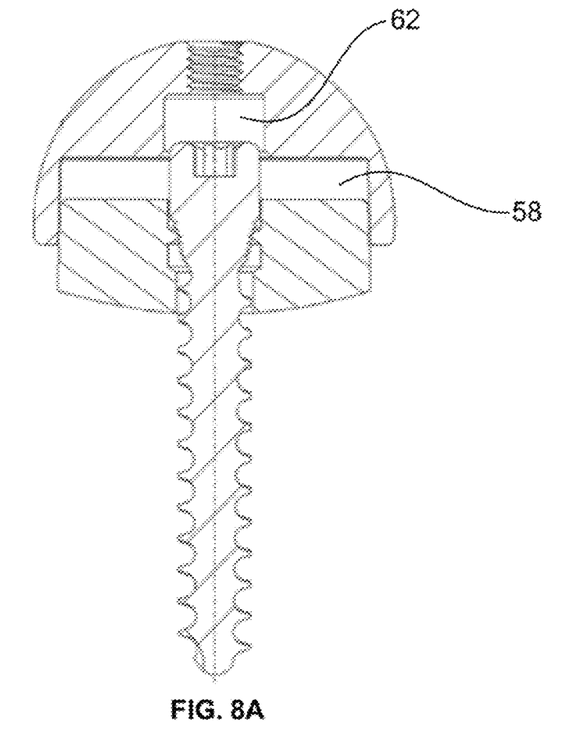
FIG. 8A is a cross-sectional view of a two-piece construct being assembled to a glenosphere.
Figure 8B:
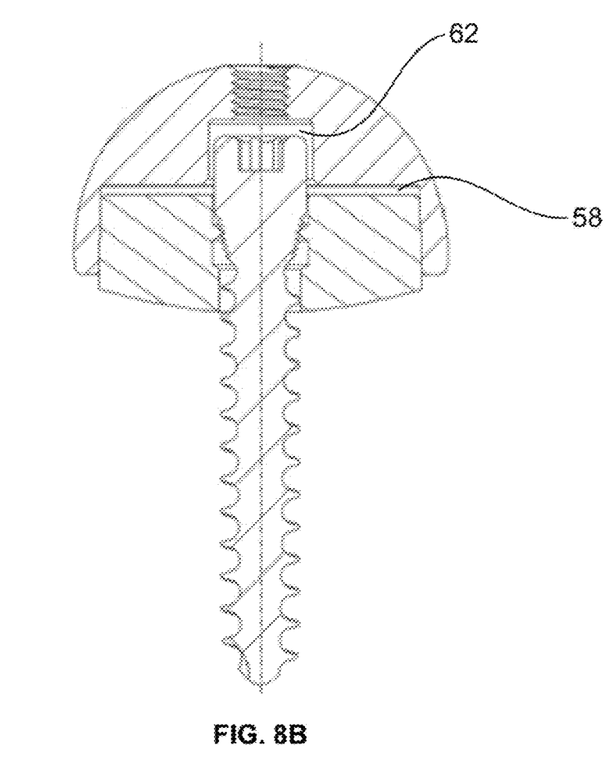
FIG. 8B is a cross-sectional view of the two-piece construct and glenosphere shown in FIG. 8A in an almost fully assembled position.

One aspect of the present invention is the assembly of glenosphere 50 with a two-piece construct 100, namely assembled central screw 80 and baseplate 20. A holding instrument (not shown) can be secured to bore 70 in order to aid the assembly of glenosphere 50 with two-piece construct 100. Alignment between baseplate 20 of two-piece construct 100 and glenosphere 50 is first introduced by the peripheral external taper of perimeter 26 of baseplate 20 and first internal bore 58 of glenosphere 50 as shown in FIG. 8A. At least a portion of head portion 82 of central screw 80 is located within pilot bore 62 prior to engagement between external taper 26 of baseplate 20 and tapered wall 59 of glenosphere 50 as shown in FIG. 8B. Pilot diameter D4 of head 82 of central screw 80 is configured to be accepted by pilot bore 62 with diameter D3 of glenosphere 50 in a slip-fit manner. The dimensions of head portion 82 of central screw and pilot bore 62 of glenosphere 50 aids in preventing glenosphere 50 from cantilevering out of its intended assembled position when external taper 26 of baseplate 20 is engaged to tapered wall 59 of glenosphere 50.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant assembly comprising:
   a first component having a top surface, a bottom surface, a side surface connecting the top and bottom surfaces, and at least one borehole extending through the top and bottom surfaces;
   a second component having first and second circumferential recesses, the first circumferential recess defining a tapered wall having a minimum diameter and terminating at an open first base surface, the second circumferential recess defining a circumferential wall having a constant diameter and terminating at a closed second base surface, the constant diameter of the circumferential wall being less than the minimum diameter of the tapered wall, the first and second circumferential recesses being in communication with one another; and
   a third component having a head portion, a body portion and a central longitudinal axis, the head portion having a top surface and a circumferential side surface, the third component configured to be received at least partially within the at least one borehole of the first component, wherein at least a portion of the head portion of the third component extends outwardly from the top surface of the first component and the body portion of the third component extends outwardly from the bottom surface of the first component when the third component is engaged to the at least one borehole of the first component such that the circumferential side surface of the head portion can be slip-fit into the second circumferential recess of the second component and into engagement with the circumferential wall thereof by aligning the central longitudinal axis of the third component with a central longitudinal axis of the second circumferential recess of the second component, the slip-fit thereby guiding the side surface of the first component into the first circumferential recess by aligning a central longitudinal axis of the first component with the central longitudinal axis of the second circumferential recess of the second component prior to engagement of the side surface of the first component with the tapered wall of the second component, the top surface of the third component defines a plane extending about the top surface lying parallel and adjacent to the closed second base surface of the second component.

2. The implant assembly of claim 1, wherein the top surface of the first component is substantially flat and the bottom surface of the first component is convex.

3. The implant assembly of claim 1, wherein the side surface of the first component is tapered and forms a circumferential perimeter of the first component, the side surface having a central longitudinal axis.

4. The implant assembly of claim 3, wherein the at least one borehole of the first component has a central axis that is coaxial with the central longitudinal axis of the side surface.

5. The implant assembly of claim 1, wherein the first component is a baseplate, the second component is a glenosphere, and the third component is a central screw.

6. The implant assembly of claim 1, further comprising a plurality of peripheral boreholes extending through the top and bottom surfaces of the first component and equally spaced around a perimeter of the top and bottom surfaces of the first component, the plurality of peripheral boreholes adapted to receive screws for fixing the first component to a glenoid cavity of a patient.

7. The implant assembly of claim 6, wherein each of the plurality of peripheral boreholes includes a ramp portion adapted to receive and engage a head of a fixation screw.

8. The implant assembly of claim 1, wherein the third component further includes a neck portion that is tapered and at least partially threaded.

9. The implant assembly of claim 8, wherein the at least one borehole includes a threaded portion adapted to engage the at least partially threaded portion of the third component.

10. The implant assembly of claim 1, wherein the tapered wall and the circumferential wall of the second component each have a longitudinal axis therethrough, the longitudinal axes being coaxial.

11. An implant assembly comprising:
a first component having a top surface, a bottom surface, a side surface connecting the top and bottom surfaces, and at least one borehole extending through the top and bottom surfaces, a distance between the top surface and bottom surface defining a first height;
a second component having first and second circumferential recesses, the first circumferential recess termination at an open first base surface and defining a tapered wall having a second height substantially equal to the first height, the second circumferential recess terminating at a closed second base surface and defining a circumferential wall having a third height, the first and second circumferential recesses being in communication with one another; and
a third component having a head portion, a body portion and a central longitudinal axis, the head portion having a circumferential side surface, the third component configured to be received at least partially within the at least one borehole of the first component such that the head portion of the third component extends outwardly from the top surface of the first component in an amount substantially equal to the third height and the body portion of the third component extends outwardly from the bottom surface of the first component,
wherein the circumferential side surface of the head portion of the third component is slidably guided by the circumferential wall of the second circumferential recess of the second component such that the central longitudinal axis of the third component is aligned with a central longitudinal axis of the second circumferential recess of the second component and the central longitudinal axis of the second circumferential recess of the second component is aligned with a central longitudinal axis of the first component prior to the side surface of the first component being engaged to the tapered wall of the second component.

12. The implant assembly of claim 11, wherein the top surface of the first component is substantially flat and the bottom surface of the first component is convex.

13. The implant assembly of claim 11, wherein the side surface of the first component is tapered and forms a circumferential perimeter of the first component, the side surface having a central longitudinal axis.

14. The implant assembly of claim 13, wherein the at least one borehole of the first component has a central axis that is coaxial with the central longitudinal axis of the side surface.

15. The implant assembly of claim 11, wherein the first component is a baseplate, the second component is a glenosphere, and the third component is a central screw.

16. The implant assembly of claim 11, further comprising a plurality of peripheral boreholes extending through the top and bottom surfaces of the first component and equally spaced around a perimeter of the top and bottom surfaces of the first component, the plurality of peripheral boreholes adapted to receive screws for fixing the first component to a glenoid cavity of a patient.

17. The implant assembly of claim 16, wherein each of the plurality of peripheral boreholes includes a ramp portion adapted to receive and engage a head of a fixation screw.

18. The implant assembly of claim 11, wherein the third component further includes a neck portion that is tapered and at least partially threaded.

19. The implant assembly of claim 18, wherein the at least one borehole includes a threaded portion adapted to engage the at least partially threaded portion of the third component.

20. The implant assembly of claim 11, wherein the tapered wall and the circumferential wall of the second component each have a longitudinal axis therethrough, the longitudinal axes being coaxial.

21. An implant assembly comprising:
a first component having a top surface, a bottom surface, and a side surface connecting the top and bottom surfaces;

a second component having a bottom surface and first and second circumferential recesses, the first circumferential recess defining a tapered wall and terminating at an open first base surface and the second circumferential recess defining a circumferential recess having a constant diameter and terminating at a closed second base surface, the first and second circumferential recesses being in communication with one another; and a third component having a head portion, a body portion and a central longitudinal axis, the head portion having a top surface and a circumferential side surface, the head portion protruding outwardly from the top surface of the first component and a body portion protruding outwardly from the bottom surface of the first component, wherein the second component is operatively coupled to the first component when the circumferential side surface of the head portion of the third component is slidably received in the second circumferential recess of the second component such that the central longitudinal axis of the third component is aligned with a central longitudinal axis of the second circumferential recess of the second component and the central longitudinal axis of the second circumferential recess of the second component is aligned with the central longitudinal axis of the first component prior to engagement between the side surface of the first component and the tapered wall of the first circumferential recess of the second component, the top surface of the third component defines a plane extending about the top surface lying parallel and adjacent to the closed second base surface of the second component.

\* \* \* \* \*